United States Patent [19]

Tanaka

[11] 4,374,175

[45] * Feb. 15, 1983

[54] NOVEL WATER-SWELLABLE FIBERS AND PROCESS FOR PRODUCING THE SAME

[75] Inventor: Koji Tanaka, Okayama, Japan

[73] Assignee: Japan Exlan Co., Ltd., Osaka, Japan

[*] Notice: The portion of the term of this patent subsequent to Nov. 6, 1999, has been disclaimed.

[21] Appl. No.: 266,055

[22] Filed: May 21, 1981

Related U.S. Application Data

[62] Division of Ser. No. 87,951, Oct. 24, 1979, abandoned.

[30] Foreign Application Priority Data

Jan. 16, 1979 [JP] Japan .................................. 54/4277

[51] Int. Cl.³ .............................................. D02G 3/00
[52] U.S. Cl. ..................................... 428/369; 8/115.5; 428/373; 428/394; 428/400
[58] Field of Search ............... 428/364, 369, 370, 371, 428/373, 374, 400, 394, 375; 8/115.5

[56] References Cited

U.S. PATENT DOCUMENTS

| | | | |
|---|---|---|---|
| 2,749,330 | 6/1956 | Banes et al. ......................... | 525/336 |
| 3,039,524 | 6/1962 | Belck et al. .......................... | 8/115.5 |
| 3,460,897 | 8/1969 | Lowes, Jr. ............................ | 8/115.5 |
| 3,728,072 | 4/1973 | Orito et al. ........................... | 8/115.5 |
| 3,733,386 | 5/1973 | Shimoda et al. ................. | 8/115.5 X |
| 3,929,946 | 12/1975 | Orito et al. ............................ | 264/41 |
| 4,143,200 | 3/1979 | Radlmann et al. ............. | 428/398 X |

FOREIGN PATENT DOCUMENTS

| | | | |
|---|---|---|---|
| 49-7526 | 1/1974 | Japan ................................... | 8/115.5 |
| 52-49394 | 4/1977 | Japan ................................... | 8/115.5 |

*Primary Examiner*—Lorraine T. Kendell
*Attorney, Agent, or Firm*—Wenderoth, Lind & Ponack

[57] ABSTRACT

The present invention relates to novel water-swellable fibers, of which at least a part of the fiber outer layer portion is composed of a hydrogel, and which fibers have latent or visualized crimps and combine a high degree of water-swellability with excellent physical properties, and to a process for producing the same. The invention also relates to an industrially advantageous process for producing novel water-swellable fibers, of which at least a part of the fiber outer layer portion is hydrogelled, said process comprising putting a prescribed amount of a specific alkali on fibers composed of an acrylonitrile polymer and then heat-treating the fibers.

6 Claims, No Drawings

NOVEL WATER-SWELLABLE FIBERS AND PROCESS FOR PRODUCING THE SAME

This application is a division of application Ser. No. 87,951, filed Oct. 24, 1979, and now abandoned.

BACKGROUND OF THE INVENTION

1. Field of the Invention

The present invention relates to novel water-swellable fibers, of which at least a part of the fiber outer layer portion is composed of a hydrophilic cross-linked polymer (hereinafter referred to as hydrogel), and which fibers have latent or visualized crimps and combine a high degree of water-swellability with excellent physical properties, and to a process for producing the same. The invention also relates to an industrially advantageous process for producing novel water-swellable fibers, of which at least a part of the fiber outer layer portion is hydrogelled, said process comprising putting a prescribed amount of a specific alkali on fibers composed of an acrylonitrile polymer (hereinafter abbreviated as AN polymer) and then heat-treating the fibers.

2. Description of the Prior Art

In recent years, polymers having a high degree of water-swellability have been used in a wide field of applications because of their particular functions. For example, attempts have been made on applications to diapers, sanitary products, etc. by utilizing the instantaneous high water-absorbing power of these polymers; or applications to soil-improving materials, instant sandbags, etc. by utilizing their high water-retentive capacity; or applications to soft contact lenses, artificial internal organs, surgical seaming materials, etc. on account of their intimate affinity to human tissues, and among these applications some are already entering on a practical stage.

As regards the water-swellable polymers (hydrogels) having possibilities of use in such a wide field of applications, cases are not few where it is preferable that they take the form of fibers to meet their use purposes, and several hydrogels in the form of fibers are known. However, although such existing natural or synthetic fibers have a certain extent of water-swellability, some have an extremely low water-swellability and others are water-soluble, and in any case they have been far from the category of water-swellable fibers which can absorb and retain an amount of water several to several hundred times their own weight, and moreover are water-insoluble. In Japanese Published patent application No. 42916/1977, there is disclosed a highly swellable fiber-shaped structure composed of acrylic fibers into which specific cross-linkages and a large amount of salt-form carboxyl groups have been introduced. However, since this fiber-shaped structure contains an extremely large amount of salt-form carboxyl groups introduced thereinto and is hydrogelled throughout the outer and inner layers of the fibers, it is provided, on one hand, with a high degree of water-swellability indeed, but on the other hand, it is so brittle that its physical properties are far from the conception of fibers. That is to say, it is the present situation that there are no water-swellable fibers having satisfactory properties, and thus the possession of a high degree of water-swellability while retaining fiber physical properties have been contradictory problems.

In such a situation, we have researched to overcome the above-mentioned fundamental difficulty and to obtain fibers having a high degree of water swellability while retaining the fiber physical properties, without using particular fibers as the starting material and without requiring a special cross-linking treatment step. As a result, we have found that, when an aqueous solution of a specific alkali-metal hydroxide is caused to act on fibers composed of an AN polymer (hereinafter abbreviated as AN fibers) in such a way that only the outer layer portion of the fibers is selectively rendered hydrophilic and cross-linked (hydrogelled), water-swellability can be advantageously given to the fibers without impairing the fiber physical properties. On the basis of this discovery, we have previously proposed an invention as Japanese patent application No. 46058/1978. However, when the fibers being treated are subjected to a hydrolytic treatment by immersion in an alkaline bath which is thought essential for causing the reaction to proceed uniformly, it is necessary to heat the whole bath, so that a large amount of energy is required. In addition, the alkaline bath is contaminated by by-products generated during the hydrolytic treatment, so that this makes it difficult to reuse the alkaline bath. Therefore, this process has required improvement from the standpoint of industrial practice.

STATEMENT OF THE INVENTION

Under such circumstances, we have found surprisingly that, by putting a prescribed amount of an aqueous solution of a specific alkali-metal hydroxide on AN fibers being treated and heating said fibers to a particular temperature to hydrolyze the fibers, it is possible to produce, in an industrially advantageous manner, novel water-swellable fibers having uniform and excellent water-swellability and fiber properties, with minimum amounts of necessary energy and alkali. Also by causing an aqueous solution of a specific alkali-metal hydroxide to act on AN fibers having latent or visualized crimps so as to selectively hydrogel only the outer layer portion of said fibers, it is possible to produce water-swellable fibers further improved in fiber properties such as bending resilience, voluminosity, etc. These findings led to the present invention.

Therefore, an object of the present invention is to provide novel water-swellable fibers having latent or visualized crimps and furthermore combining a high degree of water-swellability with excellent physical properties and a process for producing the same.

Another object of the present invention is to provide an industrially advantageous process for producing novel water-swellable fibers combining excellent water-swellability with excellent fiber properties, without the necessity of using any particular fibers as the starting material.

A further object of the present invention is to provide a process which enables continuous production of water-swellable fibers free from fiber agglutination and having uniform properties, using minimum amounts of necessary energy and alkali.

The water-swellable fibers according to the present invention attaining said objects are fibers, of which at least a part of the fiber outer layer portion is composed of a hydrogel, and which have latent or visualized crimps and moreover combine a high degree of water-swellability with excellent physical properties. Such water-swellable fibers can be advantageously produced by causing an aqueous solution of an alkali-metal hydroxide of a high concentration not less than 6.0 mol/1000 g solution or an aqueous solution of a low concentration coexisting with an electrolytic salt of a concentration not less than 0.5 mol/1000 g solution to act on AN fibers having latent or visualized crimps so as to hydrogel at least a part of the outer layer portion of said fibers, and so that said fibers with latent or visualized crimps will combine a high degree of water-swellability with excellent physical properties.

Said latter objects of the present invention can be attained by putting an alkali-metal hydroxide alone or a combination of an alkali-metal hydroxide with a hydrolytic salt or an aqueous solution of these compounds onto AN fibers so as to prepare fibers holding an alkali-metal hydroxide solution of a high concentration not less than 6.0 mol/1000 g solution or an alkali-metal hydroxide solution of a low concentration coexisting with a hydrolytic salt of a concentration not less than 0.5 mol/1000 g solution within the range of from 2 to 200%, based on the dry weight of said fibers, and heating the thus-prepared fibers to a temperature not lower than 80° C., thereby forming said fibers into such fibers wherein at least a part of the fiber outer layer portion is composed of a hydrogel.

DESCRIPTION OF PREFERRED EMBODIMENTS

As used in the present invention the term "AN polymers" is a generic term for polymers containing AN as a copolymerization component, and includes AN homopolymers; copolymers of AN with one or more ethylenically unsaturated compounds; graft copolymers of AN with other polymers such as starch, polyvinyl alcohol, etc.; and mixed polymers composed of AN polymers and other polymers such as polyvinyl chloride, polyamides, polyolefins, polystyrenes, polyvinyl alcohols, cellulose, etc. The content of AN in such AN polymers is desirably not less than 30 weight %, and more preferably not less than 50 weight %. If fibers from a polymer having an AN content less than the above-recommended limit are used as the starting material, the fibers will not be made sufficiently hydrophilic by the alkaline hydrolytic treatment, or even if made hydrophilic, the fibers will not become water-swellable. There are no particular restrictions on the kind of the above-mentioned ethylenically unsaturated compounds which are copolymerization components of the AN polymers, and on the molecular weight of said polymers, and these can be selected voluntarily to meet the demanded properties of the final product, copolymerizability of the monomer, etc. Also, as regards the process for producing the polymers and the process for forming fibers having latent or visualized crimps from the polymers, these can be selected voluntarily from known processes (for example, mono-component spinning, sheath-core composite spinning, etc.). In the present invention, as the AN fibers having latent or visualized crimps, there can be used, in addition to those produced from an AN polymer mono-component, sheath-core type composite fibers, of which the sheath component is made of an AN polymer easily hydrolyzable under the subsequent hydrolytic treatment condition and the core component is made of another AN polymer which is difficult to be hydrolyzed; or sheath-core type composite fibers, of which the sheath component is made of an easily hydrolyzable AN polymer and the core component is made of another polymer (for example, polyamide, polyolefin, etc.). Also, so far as the fibers have a cross-sectional structure in which at least a part of an AN polymer is exposed on the surface of the fibers, such fibers can be used as starting material AN fibers of the present invention. For example, there can be mentioned fibers produced by particular spinning processes, such as fibers produced by random composite spinning of two or more components (AN polymers and if desired, other polymers); so-called "sea-islands" type composite fibers; "side-by-side" bicomponent conjugated fibers; or "sandwich" type composite fibers, etc. As long as such fibers have latent or visualized crimps, they can be employed as a starting material of the present invention. Self-crimping fibers, such as those of the "side-by-side" bicomponent conjugated type, random composite spinning type, eccentric sheath-core type, "sea-islands" type, etc. have a better crimp-retaining ability in comparison with mechanically crimped fibers. These self-crimping fibers have less tendency of losing crimps under the alkali treatment condition, or if desired, their latent crimps can be visualized during alkali treatment. Therefore, it is preferable to use such self-crimping fibers as a starting material. Such self-crimping fibers can be used after visualizing crimps by means of heat treatment, etc. or without visualizing crimps, or in a latent crimps state in which the crimps once visualized have been caused to disappear by heat-stretching, etc. Also, it goes without saying that fibers given mechanical crimps to such self-crimping fibers having latent or visualized crimps can be advantageously used as a starting material of the present invention.

The crimp characteristics, latent or visualized, of the AN fibers are generally maintained under the alkali treatment condition recommended in the present invention, and therefore the crimp characteristics of the AN fibers determine the crimp characteristics of the water-swellable fibers to be finally obtained, nearly decisively. The crimp characteristics of the AN fibers are not limited so far as they have latent or visualized crimps, but it is desirable that the number of crimps ($C_n$) per 25 mm length of fibers in a crimp visualized state should be more than 3, preferably more than 5 and the crimp index ($C_i$) should be more than 5%, preferably more than 7%, from the viewpoint of properties in practical use, such as bending resilience, voluminosity, etc. of the water-swellable fiber products to be finally obtained.

The fibers thus produced can be subjected to the subsequent hydrolytic treatment whatsoever form the fibers may take, such as short fibers, long fibers, fiber tows, yarns, knitted products, woven products, or non-woven products, etc. It goes without saying that waste fibers discharged from the AN fiber production process, etc. or semi-produced fibers during said production process (for example, fibers after the heat-stretching step), can be used also as a starting material of the present invention.

In order to obtain water-swellable fibers having latent or visualized crimps and combining a high degree of water-swellability with excellent physical properties from such AN fibers, it is necessary to selectively hydrogel only the outer layer portion of the AN fibers so that the fibers can have a multiple structure composed of an outer layer whose at least a part is a hydrogel and an inner layer of an AN polymer and/or another polymer.

The degree of water-swellability of the thus-produced fibers having a dual or multiple structure ranges desirably from 3 to 300 cc/g and more preferably from 5 to 200 cc/g. Furthermore, in order that the fibers can have such a degree of water-swellability and retain sufficient physical properties, it is desirable that the amount of the salt type carboxyl groups represented by the formula —COOX (wherein X is an alkali-metal or NH$_4$) should be adjusted to a value ranging from 0.1 to 4.0 m mol/g, more preferably from 0.5 to 3.5 m mol/g. If the amount of the salt-type carboxyl groups is out of the lower limit of the recommended range, the hydrophilicity or water-absorbing capacity will be insufficient, and when the amount exceeds the upper limit of said range, the fibers will have poor physical properties and will become brittle and less flexible. As regards the kinds of the salt-type carboxyl groups, these may be an alkali-metal carboxylate such as Li-, K-, or Na-, etc. carboxylate, or NH$_4$ carboxylate, or a mixed carboxylate of two or more of these alkali-metals and NH$_4$.

The crimp characteristics which such water-swellable fibers should have are not limited so far as the fibers have latent or visualized crimps, and the crimp characteristics can be suitably decided in accordance with the use of the fibers. However, it is desirable to produce water-swellable fibers having crimp characteristics such that the number of crimps per 25 mm length (Cn) in a crimp-visualized state is not less than 3 and the crimp index (Ci) is not less than 5%, in order to improve the compressive elasticity, bulkiness, etc. of the products to be finally obtained. In the case where the water-swellable fibers are subjected to processing, such as spinning, like usual textile fibers, it is desirable to decide the characteristics of visualized crimps such that the number of crimps (Cn) is within the range of 5 to 15 and the crimp index (Ci) within the range of 5 to 25%.

A detailed explanation on the method of hydrolyzing the AN fibers will be made in the following. So far as it is possible to finally obtain water-swellable fibers having latent or visualized crimps, consisting of an outer layer portion wherein at least a part is a hydrogel and an inner layer portion of an AN polymer, there are no restrictions on the method of hydrolysis. However, in the present invention, the following means is employed which is a one-step hydrolyzing-cross-linking process that can selectively hydrogel only the outer layer portion of the AN fibers.

Namely, there is employed either a process (hereinafter referred to as "A" process) in which an aqueous solution of an alkali-metal hydroxide of a high concentration not less than 6.0 mol/1000 g solution is caused to act on the AN fibers, or another process (hereinafter referred to as "B" process) in which an aqueous solution of an alkali-metal hydroxide of a low concentration coexisting with an electrolytic salt of a concentration not less than 0.5 mol/1000 g solution is caused to act on the AN fibers.

Upon employing the A process, if an aqueous alkaline solution of a concentration less than 6.0 mol/1000 g solution is cause to act, the AN fibers are made hydrophilic indeed by the hydrolytic reaction but become water-soluble, and it is impossible to form a hydrogel outer layer to which the present invention is directed. The present invention can be more effectively realized by using an aqueous alkaline solution in the range of concentration of from 6.25 to 8.85 mol/1000 g solution, more preferably from 6.25 to 8.50 mol/1000 g solution. Under conditions exceeding the upper limit of the preferred range, the activity of the alkali-metal hydroxide is lowered, so that in order to increase the reaction rate, a high-temperature treatment is required, and also the treatment for the removal of remaining alkali becomes then difficult. Therefore, such conditions are not desirable from the viewpoint of practical use.

Upon employing the B process, if the coexisting salt is of a low concentration less than 0.5 mol/1000 g solution, the An fibers are made hydrophilic by the hydrolytic reaction indeed, but most of the fibers become water-soluble, and therefore it is impossible to form a hydrogel outer layer portion by the one-step process using an aqueous alkaline solution of a low concentration. The present invention can be more advantageously practiced industrially by using an aqueous solution of an alkali-metal hydroxide of a concentration of from 0.25 to 6.0 mol/1000 g solution, preferably 0.5 to 5.0 mol/1000 solution, containing an electrolytic salt of a concentration of 1.0 mol/1000 g solution or higher.

The alkali-metal hydroxides used in the present invention include hydroxides of alkali-metals such as Na, K, Li, etc. and mixtures of such hydroxides. As the electrolytic salts, any salts can be used so far as they are stable under the alkali treatment condition. Such salts include those salts whose cationic component is an alkali-metal (such as Na, K, Li, etc.) or an alkali-earth metal (such as Be, Mg, Fe, Co, Ni, etc.) or NH$_4$, and whose anionic component is an acid radical (such as hydrochloride, sulfate, nitrate, chromate, dichromate, chlorate, hypochlorite, organic carboxylate, organic sulfonate, etc.) and mixtures of two or more of these salts. When an electrolytic salt whose cationic component is a divalent or higher valent element is used, the resulting hydrogel outer layer is liable to agglomerate or unite with each other, and furthermore the degree of water-swellability is lowered. Therefore, it is preferable to use a salt whose cationic component is an alkali-metal or NH$_4$. As solvents to replace water, aqueous mixed solvents composed of water and water-miscible organic solvents such as methanol, ethanol, propanol, 2-methoxyethanol, dimethylformamide, dimethyl sulfoxide, etc. can be used so far as such mixed solvents do not dissolve the AN fibers being treated. If necessary, it is possible to add other organic or inorganic substances.

If the AN fibers are subjected to an alkaline hydrolytic treatment under known conditions, substantially only water-soluble polymer is formed, but when the particular conditions of the A or B process recommended in the present invention are employed, hydrogel is formed in one-step and in high yields. This is extremely different from the results expected from the reaction under known conditions. Although the reaction mechanisms involved have not yet accounted for in detail, a possible supposition may be that, accompanied with the hydrolytic reaction of nitrile groups in the outer layer of the fibers, side-reactions to form intermolecular cross-likages or intramolecular ring structures will proceed in a peculiar manner under the above-mentioned conditions.

It is impossible to fixedly prescribe the reaction conditions (including the temperature and/or treating time conditions) upon causing an aqueous alkaline solution as mentioned above to act on the AN fibers, because the preferred range of conditions is different depending on the form of the polymer, the fine structure, such as crystallinity, of the polymer, the concentration of alkali, etc.

However, from the consideration of the fact that a higher temperature will generally increase the reaction rate and enhance the treating effect more advantageously, it is recommended that a temperature not lower than 50° C., preferably not lower than 80° C. should be used, whereby the present invention can be realized more effectively.

Upon producing fibers wherein at least a part of the fiber outer layer portion is a hydrogel by causing an aqueous alkaline solution to act on the AN fibers as mentioned above, it is important to control the amount of salt-type carboxyl groups (—COOX) contained therein which have a particular close relation with the degree of water-swellability and physical properties of the fibers to be finally obtained. The method for controlling the amount of salt type carboxyl groups can be varied depending on the kind of the AN fibers used, namely the composition, crystallinity, single-filament denier, etc. thereof, and/or on the condition for the hydrolytic treatment, namely the concentration of the alkali-metal hydroxide and/or the electrolytic salt, the temperature of hydrolysis, the amount of the aqueous alkaline solution reative to the amount of the fibers to be treated, the treating time, etc., and therefore it is difficult to prescribe the condition fixedly. However, by controlling the hydrolytic treating time to not more than 40 minutes, preferably within the range of from 2 to 30 minutes, the object of the present invention can be easily attained. If fibers composed of a single component of an AN polymer are subjected to the hydrolytic treatment for a long time exceeding the recommended range of the present invention, water-swellable fibers having satisfactory physical properties cannot be obtained, because the inner layer of the AN polymer will be then completely lost, or even it remains its amount will be little, or the border line between the outer layer and the inner layer will become unclear. Therefore, such a treatment for a long time is not desirable.

In either the A or B process, it is advantageous from the industrial viewpoint to cause the AN fibers being treated to hold the above-mentioned aqueous alkaline solution and then to hydrolyze the fibers by heating. It is necessary that the amount of the alkaline solution to be held by the fibers should be controlled to within the range of 2 to 200%, preferably 5 to 100%, based on the dry weight of the fibers. In case the amount of the alkaline solution held by the fibers is less than 2%, it will be impossible to produce fibers having a desired water-swellability even if the particular aqueous alkaline solution recommended in the present invention is caused to act on the fibers. If the amount exceeds 200%, not only the improving effect in water-swellability reaches the ceiling, but also there will be a difficulty in removing the excess alkali.

As the methods of causing the fibers to hold the prescribed amount of the aqueous alkaline solution, there is no restriction on the methods if the method used is able to control the amount to within the range recommended in the present invention. For example, there can be mentioned a method wherein the AN fibers to be treated, in a water-containing state, are caused to hold a prescribed amount of powder of an alkali-metal hydroxide, singly or in combination with powder of an electrolytic salt; a method wherein the fibers to be treated, in a dry state or a water-containing state, are sprayed with an aqueous alkaline solution, and if desired, the fibers are removed from the solution by a cetrifuge, or by pressing after immersing the fibers in an aqueous solution; etc.

It is desirable from the industrial viewpoint that the AN fibers under treatment in a dry state are caused to hold a prescribed amount of an aqueous alkaline solution of a prescribed concentration prepared beforehand, because the amount of the aqueous alkaline solution held by the fibers and the concentration (amount held by the fibers) of an alkali-metal hydroxide or electrolytic salt can be easily controlled.

The fibers which have been caused to hold a prescribed amount of an aqueous alkaline solution are then subjected to hydrolytic treatment by heating.

Although it is difficult to decide the temperature condition of this heating fixedly, it is advisable to employ a temperature above 80° C., preferably between 100° and 250° C., because in general the reaction rate is increased with the elevation of temperature to more effectively attain the treating effect. If a wet-heat atmosphere or a heating means such as saturated steam, superheated steam, etc. is employed as the heating atmosphere, this is advantageous because easy temperature controlling, high efficiency of heating and uniform hydrolytic or cross-linking reaction can be attained. Of course, heating means such as heating rollers, heating plates may be suitably used.

Since the heating time can be varied depending on the kind of AN fibers to be treated, amount of the aqueous alkaline solution held by the fibers, heating temperature, or on the degree of water-swellability to be attained, it is difficult to decide it fixedly. However, by employing a heating temperature between 100° and 250° C. with a heat treatment time preferably less than 30 minutes, more preferably between 5 seconds and 20 minutes, the water-swellable fibers of the present invention, of which only the outer layer portion is hydrogelled selectively, can be produced in an industrially advantageous manner. The employment of such a preferable treatment condition enables continuous production of the water-swellable fibers of the present invention, so that this process is very important from the industrial standpoint. It goes without saying that water-swellable fibers having no crimps can be also produced by causing the aqueous alkaline solution to act on AN fibers having no crimps.

As the methods of causing the aqueous alkaline solution to act on the AN fibers, there can be mentioned various known immersion treatment methods of a non-uniform system, such as a method wherein short fibers cut into desired lengths are suspended in the aqueous solution and are stirred with a shearing apparatus such as a screw-type stirrer, mixer, etc. or kneaded with a kneader; a method wherein continuous fibers in the form of long fibers, fiber tows, yarns, knitted or woven fabrics, non-woven fabrics, etc. are caused to travel through said aqueous solution, in a tensioned or tension-free state; a method wherein short fibers, long fibers, etc. are put into a net-shaped container and are shaken in said aqueous solution; etc.

The water-swellable fibers thus obtained are washed with water to remove alkali-metal hydroxide remaining in said fibers. Thereafter, if necessary, the fibers are subjected to a treatment to change the salt-type carboxyl groups to alkali-metal salt or ammonium salt by a known method, and if desired the fibers are subjected to a drying treatment to form dry fibers.

In this way, it is possible to obtain water-swellable fibers, of which at least a part of the fiber outer layer portion is composed of a hydrogel and which have latent or visualized crimps. To our surprise, the fibers have a water-swellability of from 3 to 300 cc/g, preferably from 5 to 200 cc/g, and besides, as regards fiber physical properties such as dry or wet strength, dry or wet elongation, knot strength, etc., the fibers can almost stand comparison with ordinary AN fibers for textile use (for example, dry-strength: 2.0 g/d or more; wet-strength: 1.5 g/d or more). In addition, since the inner layer portion of the fibers is composed of an AN polymer, etc., the fibers do not show any dimensional change in the lengthwise direction even in a swollen state.

Thus it is a striking advantage of the present invention that the water-swellable fibers of the present invention composed of a dual or multiple structure and having latent or visualized crimps exhibit, in addition to the excellent water-swellability, excellent physical properties such as strength, elongation, flexibility, bending resilience, etc. because the fibers have an inner layer composed of an AN polymer and/or another polymer, and that the fibers display still more excellent characteristics in various properties such as compressive elasticity, bulkiness, etc. of the final product, because the fibers have crimps.

It is also a striking advantage of the present invention that fibers with a high degree of water-swellability and excellent physical properties can be obtained from ordinary AN fibers or waste fibers discharged from the production process of such fibers, by a one-step treatment process with an aqueous alkaline solution, without requiring the use of fibers composed of a polymer of a particular composition containing a cross-linkable monomer, etc. as a copolymerization component, and that the degree of water-swellability and physical properties of the thus-obtained fibers can be easily controlled by regulating the condition of the hydrolytic treatment.

The water-swellable fibers of the present invention which combine such a high degree of water-swellability with excellent physical properties, are spun or made into paper, in their single form or in mixture with existing natural, semi-synthetic or synthetic fibers to produce novel textile materials or products having excellent moisture-absorbing power, water-absorbing power, and water retaining power, which can be used as diapers, sanitary products, filter papers, materials for removing water from organic solvents which are not miscible with water, sealing materials, cation-exchanging fibers, or like existing hydrogel powder or grains, as instant sandbags, artificial soil, artificial sphagnum moss, materials for keeping warm or cold, etc.

For a better understanding of the present invention, examples are set forth in the following, but it is to be understood that the scope of the invention is by no means limited by the description of these examples, in which all percentages and parts are by weight unless otherwise indicated.

The degree of water-swellability, the amount of salt-type carboxyl groups (—COOX), bulkiness and compressive elasticity are measured and calculated by the following methods:

(1) Degree of water-swellability (cc/g)

About 0.1 gram of sample fibers is immersed in pure water and the water is maintained at 25° C. After 24 hours, the fibers are wrapped in a nylon filter cloth (200 mesh) and the water remaining about the fibers is removed by a centrifuge (3 G×30 minutes, wherein G represents the acceleration of gravity). The weight of the sample fibers thus prepared is measured ($W_1$ g). The sample is then dried in a vacuum drier at 80° C. until it reaches a constant weight ($W_2$ g). From the above measurement results, the degree of water-swellability is calculated by the following formula. Accordingly, the present degree of water-swellability is a numerical value showing how many times of water based on the fibers' own weight can be absorbed and retained by the fibers.

$$\text{Degree of water-swellability} = (W_1 - W_2)/W_2$$

(2) Amount of —COOX groups (m mol/g)

About one gram of thoroughly dried sample fibers is weighed accurately (X g). After 200 ml water is added to this sample, an aqueous 1 N hydrochloric acid solution is added while heating to 50° C. to adjust the pH to 2. Then a titration curve is obtained in the usual way using an aqueous 0.1 N caustic soda solution. From this titration curve, the amount of caustic soda solution consumed by the carboxyl groups is obtained (Y cc). From the result of the above measurement, the amount of the carboxyl groups is calculated by the following formula:

$$\text{Amount of —COOX groups} = 0.1 \, Y/X$$

If polyvalent cations are contained, the above formula must be corrected by obtaining the amount of these cations in the usual way.

(3) Bulkiness (cm$^3$/g) and compressive elasticity (g/cm)

After about 10 g of the sample fibers are opened and loosened, the fibers are piled up into a square (10×10 cm) to prepare a test piece. The weight of the test piece is measured ($W_3$ g). The test piece is compressed at a rate of 100 mm/min to a compressive load of 5 g/cm$^3$ in a constant-rate compression tester and then the load is removed. This cycle is repeated three times. From the compressive curve at the third compression cycle, the thickness ($h_o$ cm) of the test piece upon the initial loading of 0.5 g/cm$^3$ is obtained, and the bulkiness is calculated by the following formula:

$$\text{Bulkiness} = (10 \times 10 \times h_o)/W_3$$

The test piece which experienced the three times repetition of compression and load removal is further compressed to a load of 50 g/cm$^3$. From this compression curve, the amount of compression work done (compressive elasticity) is calculated as an integrated value of the thickness of the test piece and the compressive load.

EXAMPLE 1

Five parts of AN composite fibers of side-by-side bicomponent conjugated type (Japan Exlan Industry; single-filament denier: 6 d; filament length; 51 mm) were immersed in 95 parts of a 30% aqueous caustic soda solution (7.5 mol/1000 g solution), and were boiled for 10 minutes under stirring. After the alkali remaining in the fibers was removed by washing with water, the fibers were dried to form white or slightly yellowish water-swellable fibers (I). The fibers thus obtained were insoluble in water. When the fibers (I) in a water-swollen state were squeezed through the hand, the core portion of the AN polymer remained. The fibers contained 2.6 m mol/g —COONa groups.

In Table 1 are shown several physical properties of the fibers (I) in comparison with the corresponding physical properties of the AN fibers before treatment.

TABLE 1

|  | Present invention Water-swellable fibers (I) | Reference values AN fibers before treatment |
|---|---|---|
| Degree of water-swellability (cc/g) | 156 | 0.2 |
| Cn (number/25 mm) | 13 | 14* |
| Ci (%) | 32 | 35* |
| Dry strength (g/d) | 2.g | 3.4 |
| Dry elongation (%) | 29.0 | 40.0 |
| Wet strength (g/d) | 2.2 | 3.0 |
| Wet elongation (%) | 25.0 | 42.0 |
| Knot strength (g/d) | 2.2 | 2.7 |

*Values after visualization of crimps by boiling the fibers for 10 minutes

As apparent from the results in Table 1, it will be understood that the water-swellable fibers (I) according to the present invention, in spite of having excellent water-swellability, are maintained at a level not inferior to the reference values of the AN fibers before treatment, both in crimp characteristics and in strength and elongation.

For comparative purposes, the same treatment was performed according to the above formulation except that an aqueous 10% (2.5 mol/1000 g solution) or 23% (5.75 mol/1000 g solution) caustic soda solution was used. In both cases, the AN fibers being treated were dissolved in the aqueous solution and formed a viscous solution. Thus, it was impossible to form water-swellable fibers of the present invention when an aqueous caustic soda solution of such a low concentration was used singly.

On the other hand, when the same treatment was performed according to the above formulation except that a 35% aqueous caustic potash solution (6.25 mol/1000 g) was used in place of the above caustic soda solution, there were obtained white or slightly yellowish fibers substantially insoluble in water and having water-swellability and crimps.

EXAMPLE 2

Each of 5 parts of the AN composite fibers of side-by-side bicomponent conjugated type described in Example 1 (however in this case fiber length 10 mm), monocomponent AN fibers given mechanical crimps (AN=90%, single-filament denier 6 d; fiber length 10 mm; Cn=9.0, Ci=10.0) and the above mono-component fibers but not given crimps, was immersed in 95 parts of a 10% aqueous caustic soda solution (2.5 mol/1000 g solution) coexisting with 20% sodium sulfate (1.5 mol/1000 g solution), and three kinds of water-swellable fibers (II–IV) were produced according to the formulation in Example 1. All of the three kinds of fibers thus obtained were insoluble in water, and it was confirmed that the core portion of the AN polymer remained.

The results of measuring several physical properties of the fibers are shown in Table 2.

TABLE 2

| Water-swellable fibers | II | III | IV |
|---|---|---|---|
| Degree of water-swellability (cc/g) | 150 | 145 | 147 |
| Cn (number/25 mm) | 12.5 | 9.0 | 0 |
| Ci (%) | 32.0 | 9.8 | 0 |
| Bulkiness (cm³/g) | 84 | 53 | 12 |
| Compressive elasticity (g/cm) | 61 | 33 | 8 |

As apparent from the results in Table 2, the water-swellable fibers having crimps (II and III) are remarkably improved in voluminosity and bending resilience in comparison with the water-swellable fibers having no crimps (IV). Such a tendency of improving the properties are most remarkable in the fibers which have started from the self-crimping fibers (II, namely the above-mentioned composite fibers).

When the hydrolytic treatment time for the above bicomponent conjugated fibers was prolonged to one hour, the resulting fibers (V) contained 8.4 m mol/g —COONa groups and had a very high degree of water-swellability of 310 cc/g. However, the fibers were very brittle and when the fibers were squeezed through the hand in a water-swollen state, it was observed that the core portion of the AN polymer was completely lost.

EXAMPLE 3

The AN composite fibers described in Example 2 were treated in the same way as in Example 2 except that, in place of 20% sodium sulfate, sodium nitrate was used and that the concentration of the latter salt and that of caustic soda were varied as shown in Table 3. All of the thus-obtained ten kinds of water-swellable fibers (VI–XV) had crimps.

The water-swellability and the amount of —COONa groups of the ten kinds of the water-swellable fibers thus obtained (VI–XV) were measured. The results are shown in Table 3.

TABLE 3

| Sample no. | Sodium nitrate concentration (mol/1000 g solution) | Caustic soda concentration (mol/1000 g solution) | Water-swellability (cc/g) | Amount of —COONa groups (m mol/g) |
|---|---|---|---|---|
| VI | 6.0 | 2.5 | 48 | 1.7 |
| VII | 5.0 | 2.5 | 72 | 1.8 |
| VIII | 4.0 | 5.0 | 203 | 3.5 |
| IX | 4.0 | 2.5 | 148 | 1.9 |
| X | 4.0 | 0.75 | 55 | 0.8 |
| XI | 4.0 | 0.25 | 1 | — |
| XII | 3.0 | 2.5 | 151 | 1.8 |
| XIII | 1.0 | 1.25 | 103 | 1.5 |
| XIV | 0.6 | 1.25 | 22 | 1.3 |
| XV | 0.4 | 1.25 | 8 | 1.3 |

The results in Table 3 shows that, when the concentration of the salt to coexist in the aqueous alkaline solution is less than the range recommended in the present invention (Sample no. XV), only fibers of a low degree of water-swellability are obtained. In this case, since a large amount of water-soluble polymer was produced, the yield of water-swellable fibers was so low that it was about 40%. In the case where the alkali concentration was extremely low (Sample no. XI), it was impossible to obtain fibers of a desired degree of water-swellability. It is apparent from Sample nos. VI, VII, IX, and XII that fibers of various degrees of water-swellability can be produced by varying the salt concentration even though the alkali concentration remains constant.

EXAMPLE 4

When AN composite fibers of side-by-side bicomponent conjugated type (single-filament denier 2.5 d; Cn after boiling for 10 minutes 15/25 mm; Ci 37%) were treated in a 30% aqueous caustic soda solution under a tension which gave a Ci of 13% (treating temperature 95° C.; treating time 25 minutes), white or slightly yellowish water-swellable fibers (XVI) having a water-swellability of 37 cc/g were obtained. When the fibers thus obtained (XVI) having crimps (Cn=11/25 mm;

Ci=13%) were subjected to carding, there was no problem both in the opening properties of the fibers and in the interwining properties.

EXAMPLE 5

After AN fibers (single-filament denier 3 d; fiber length 51 mm; inherent viscosity in DMF at 30° C. 1.3) consisting of 90% AN and 10% MA were opened, a 30% (7.5 mol/1000 g solution) aqueous caustic soda solution was sprinkled uniformly on the fibers so that the fibers could hold 20%, based on the dry weight of the fibers, of the solution.

The fibers were then put into an autoclave, and after the fibers were heated therein in saturated steam at 115° C. for 10 minutes, the fibers were removed from the remaining alkali by washing with water and dried to produce white or slightly yellowish water-swellable fibers (XVII).

The fibers (XVII) thus obtained were insoluble in water. When the fibers were squeezed through the hand in a water-swollen state, it was observed that the core portion of the AN polymer remained, and only the outer layer of the AN fibers was hydrogelled. The fibers (XVII) contained 2.3 m mol/g —COONa groups. The results of measurement of several physical properties of the water-swellable fibers (XVII) are shown in Table 4 in comparison with the corresponding values of the AN fibers before treatment.

TABLE 4

|  | Present invention Water-swellable fibers (XVII) | Reference values AN fibers before treatment |
| --- | --- | --- |
| Water-swellability (cc/g) | 140 | 0.2 |
| Dry strength (g/d) | 2.7 | 3.2 |
| Dry elongation (%) | 35.0 | 40.0 |
| Wet strength (g/d) | 2.4 | 2.7 |
| Wet elongation (%) | 34.0 | 43.0 |
| Knot strength (g/d) | 2.5 | 3.0 |

It is apparent from Table 4 that the water-swellable fibers (XVII) according to the present invention, in spite of having excellent water-swellability, are maintained at a level substantially not inferior to the reference values of the AN fibers before treatment, both in strength and in elongation.

On the other hand, as a comparative example, when the treatment was carried out in accordance with the above-mentioned formulation except that a 10% or 23% aqueous caustic soda solution was used, the AN fibers being treated formed only a water-soluble polymer in both cases, and thus it was impossible to form water-swellable fibers of the present invention when an aqueous solution of caustic soda only of such a low concentration was used.

As a further comparative example, the AN fibers holding the above aqueous caustic soda solution were air-dried without subjecting the fibers to heat treatment, and were allowed to stand at room temperature for one day. When the fibers thus obtained were measured for the water-swellability, it was found that the fibers were not given any water-swellability.

When the same treatment was carried out except that a 40% (7.1 mol/1000 g solution) aqueous caustic potash solution was used in place of the above caustic soda solution, white or slightly yellowish water-swellable fibers which were substantially insoluble in water were obtained.

EXAMPLE 6

Each of the aqueous solutions with various concentrations of sodium nitrate and caustic soda as shown in Table 5 was sprinkled on AN fibers (single-filament denier 6 d; fiber length 38 mm; inherent viscosity in DMF at 30° C. 1.3) consisting of 90% AN and 10% MA so that the fibers could hold 30%, based on the fibers, of the solution. Thereafter, the fibers were heated, washed with water, and dried according to the formulation described in Example 5 and nine kinds of fibers (XVIII-XXVI) were obtained.

The water-swellability and the amount of —COONa groups of the fibers thus obtained (XVIII–XXVI) were measured. The results are also shown in Table 5.

TABLE 5

| Sample no. | Sodium nitrate concentration (mol/1000 g solution) | Caustic soda concentration (mol/1000 g solution) | Water-swell-ability (cc/g) | Amount of —COONa groups (m mol/g) |
| --- | --- | --- | --- | --- |
| XVIII | 6.0 | 2.5 | 35 | 1.4 |
| XIX | 5.0 | 2.5 | 63 | 1.5 |
| XX | 4.0 | 5.0 | 130 | 2.2 |
| XXI | 4.0 | 2.5 | 85 | 1.6 |
| XXII | 4.0 | 1.0 | 41 | 0.5 |
| XXIII | 4.0 | 0.4 | 1 | — |
| XXIV | 3.0 | 2.5 | 116 | 1.4 |
| XXV | 1.0 | 2.5 | 30 | 0.9 |
| XXVI | 0.4 | 2.5 | 10 | 0.5 |

As shown in Table 5, when the concentration of the salt coexisting in the aqueous alkaline solution was less than the range recommended in the present invention (XXVI), the amount of water-soluble polymer generated was increased remarkably, so that the yield of the water-swellable fibers was extremely low (about 10%). When the concentration of the alkali was extremely low (XXIII), even if a recommended amount of the salt was caused to coexist, only fibers of an extremely low water-swellability were obtained. It was found that by varying the alkali concentration or the concentration of the salt to coexist, fibers (XVIII–XXII, XXIV and XXV) having various degrees of water-swellability could be produced.

EXAMPLE 7

In the process for the production of the water-swellable fibers (XVII) described in Example 5, only the amount of the 30% aqueous caustic soda solution to be held by the fibers was varied as shown in Table 6 to produce six kinds of fibers (XXVII–XXXII).

The water-swellability and the amount of —COONa groups of the fibers (XXVII–XXXII) were measured. The results are also shown in Table 6.

TABLE 6

| Sample no. | Amount of alkali held by the fibers (%) | Water-swell-ability (cc/g) | Amount of —COONa groups (m mol/g) |
| --- | --- | --- | --- |
| XXVII | 1 | 0.4 | — |
| XXI | 3 | 24 | 0.2 |
| XXIX | 50 | 145 | 2.2 |
| XXX | 100 | 162 | 2.5 |
| XXXI | 150 | 155 | 2.4 |
| XXXII | 210 | 157 | 2.6 |

As apparent from the results in Table 6, when the amount of alkali held by the fibers was less than the recommended range (XXVII), substantially no water-swellability was observed. The water-swellability of the fibers was increased with the increase of the amount of alkali held by the fibers, but such an increasing effect of water-swellability shows a tendency of hitting the peak.

When an extremely large amount of alkali was given to the fibers (XXXII), a large amount of acid and a long time were required for the removal of excess alkali.

EXAMPLE 8

AN fibers (single-filament denier 15 d; filament length 50 mm; inherent viscosity in DMF at 30° C. 1.5) consisting of 80% AN and 20% vinyl acetate were treated according to the formulation described in Example 5 except that the heating temperature and the treating time were 120° C. and 5 minutes, respectively. Water-swellable fibers (XXXIII) were obtained which were white or slightly yellowish and had a degree of water-swellability of 140 cc/g.

EXAMPLE 9

The AN composite fibers described in Example 4 were treated according to the formulation described in Example 5. Fibers (XXXIV, Cn=14/25 mm, Ci=35%) having a degree of water-swellability of 105 cc/g were obtained.

What is claimed is:

1. Water-swellable acrylonitrile polymer fibers which contain salt-type carboxyl groups represented by the formula —COOX wherein X is an alkali-metal or NH4 in an amount of from 0.1 to 4.0 mol/g, and which are produced by treating acrylonitrile polymer fibers having latent or visualized crimps with (a) an aqueous alkali-metal hydroxide solution of a high concentration not less than 6.0 mol/1000 g solution or (b) an aqueous alkali-metal hydroxide solution of a low concentration coexisting with an electrolytic salt of a concentration not less than 0.5 mol/1000 g solution thus rendering the outer layer portion of said fibers hydrophilic and cross-linked, wherein at least a part of the fiber outer layer portion is composed of a hydrogel and the remainder is composed of an acrylonitrile polymer and/or another polymer, the resultant fibers having latent or visualized crimps and combining a high degree of water-swellability of 3 to 300 cc/g with excellent physical properties.

2. A process for producing novel water-swellable fibers characterized in that an aqueous alkali-metal hydroxide solution of a high concentration not less than 6.0 mol/1000 g solution or an aqueous alkali-metal hydroxide solution of a low concentration coexisting with an electrolytic salt of a concentration not less than 0.5 mol/1000 g solution is caused to act on fibers of an acrylonitrile polymer in order to render the outer layer portion of said fibers hydrophilic and cross-linked, whereby said fibers are formed into fibers, of which at least a part of the fiber outer layer portion is composed of a hydrophilic cross-linked polymer, and which have latent or visualized crimps and combine a high degree of water-swellability with excellent physical properties.

3. The process as claimed in claim 2 wherein, as said aqueous alkali-metal hydroxide solution of a low concentration, an aqueous alkali-metal hydroxide solution of a concentration from 0.25 to 6.0 mol/1000 g solution coexisting with an electrolytic salt of a concentration not less than 0.5 mol/1000 g solution is used.

4. The process as claimed in claim 2 wherein salt type carboxyl groups represented by the formula —COOX (wherein X is an alkali-metal or NH4) are introduced into the fibers in an amount of from 0.1 to 4.0 m mol/g.

5. A process for producing water-swellable acrylonitrile fibers which comprises contacting said acrylonitrile fibers with an aqueous alkali-metal hydroxide solution of a high concentration not less than 6.0 mol/1000 g solution or an aqueous alkali-metal hydroxide solution of a low concentration coexisting with an electrolytic salt of a concentration not less than 0.5 mol/1000 g solution such that the fiber contains said solution within the range of from 2–200%, based on the dry weight of the fibers, whereby salt-type carboxyl groups represented by the formula —COOX, in which X is an alkali-metal or NH4 are introduced into the fibers in an amount of from 0.1 to 4.0 m mol/g fibers and the thus-prepared fibers are heated to a temperature not lower than 80° C., whereby said fibers are formed such that at least a part of the fiber outer layer portion is composed of a hydrophilic cross-linked polymer.

6. The process as claimed in claim 5 wherein the fibers are heated in a wet-heat atmosphere to a temperature of from 100° to 250° C.

* * * * *